US010938790B2

(12) United States Patent
Brathwaite

(10) Patent No.: US 10,938,790 B2
(45) Date of Patent: Mar. 2, 2021

(54) SECURITY SYSTEM AND METHOD

(71) Applicant: Carlos Enrique Brathwaite, Brooklyn, NY (US)

(72) Inventor: Carlos Enrique Brathwaite, Brooklyn, NY (US)

( * ) Notice: Subject to any disclaimer, the term of this patent is extended or adjusted under 35 U.S.C. 154(b) by 232 days.

(21) Appl. No.: 16/377,899

(22) Filed: Apr. 8, 2019

(65) Prior Publication Data

US 2020/0322318 A1 Oct. 8, 2020

(51) Int. Cl.
| | |
|---|---|
| *H04L 29/06* | (2006.01) |
| *G16B 15/00* | (2019.01) |
| *G06F 16/13* | (2019.01) |
| *G16B 45/00* | (2019.01) |
| *G06F 21/60* | (2013.01) |
| *H04L 9/08* | (2006.01) |
| *G16B 30/00* | (2019.01) |

(52) U.S. Cl.
CPC .......... *H04L 63/0428* (2013.01); *G06F 16/13* (2019.01); *G06F 21/602* (2013.01); *G16B 15/00* (2019.02); *G16B 30/00* (2019.02); *G16B 45/00* (2019.02); *H04L 9/0861* (2013.01)

(58) Field of Classification Search
CPC ... H04L 63/0428; H04L 9/0861; G06F 16/13; G06F 21/602; G16B 15/00; G16B 45/00; G16B 30/00

USPC .......................................................... 713/165
See application file for complete search history.

(56) References Cited

U.S. PATENT DOCUMENTS

| | | | |
|---|---|---|---|
| 9,449,199 B2* | 9/2016 | Dominguez | G06F 21/84 |
| 2013/0028419 A1* | 1/2013 | Das | 380/259 |
| 2013/0046994 A1* | 2/2013 | Shaw | H04L 9/0866 713/189 |
| 2013/0254537 A1* | 9/2013 | Bogorad | G06F 21/602 713/165 |
| 2018/0034784 A1* | 2/2018 | Sinclair | H04L 9/12 |
| 2018/0139055 A1* | 5/2018 | Brathwaite | H04L 9/0656 |

\* cited by examiner

*Primary Examiner* — Dereena T Cattungal
(74) *Attorney, Agent, or Firm* — Stadler IP Law PLLC

(57) ABSTRACT

A security system and method for improving the security of a file/data transmitted from a special purpose user computer to a recipient special purpose computer. A special purpose computer having an individualized encryption software application server that runs individualized encryption software is provided, along with an amino acid database generator having an amino acid database storing natural and/or synthetic amino data. The individualized encryption software applicant server sends a request to the secure amino acid database generator producing the mathematical characteristics of the natural and synthetic amino acids. This is used to construct an amino acid base layer. The amino acid base layer is folded into two or three dimensional shapes and have values assigned to them, and a secret key is provided such that the transmission cannot be opened by a recipient unless he or she has the key and the values associated with the folded amino acids.

19 Claims, 7 Drawing Sheets

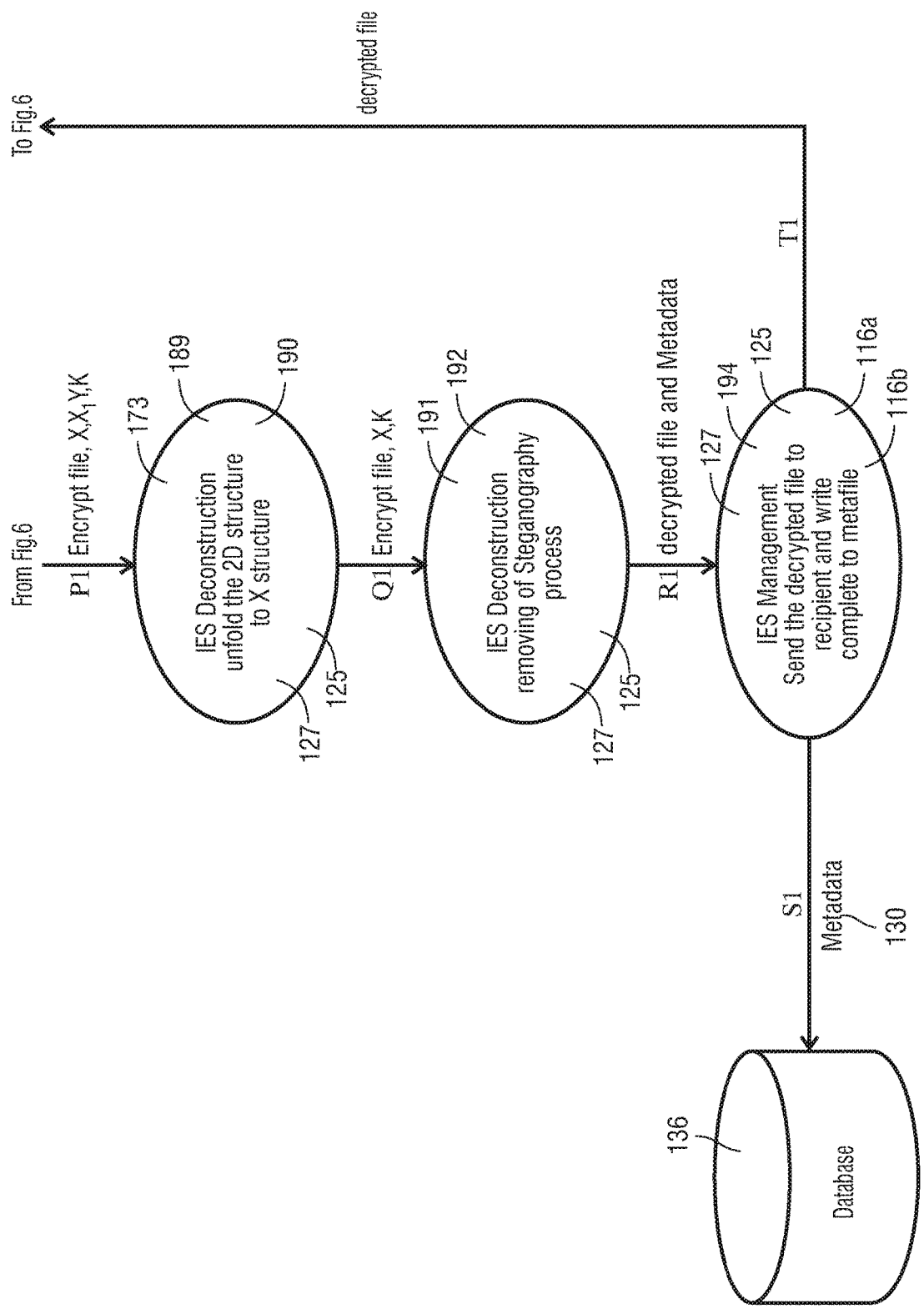

SECURITY SYSTEM AND METHOD

BACKGROUND

Figure 1:
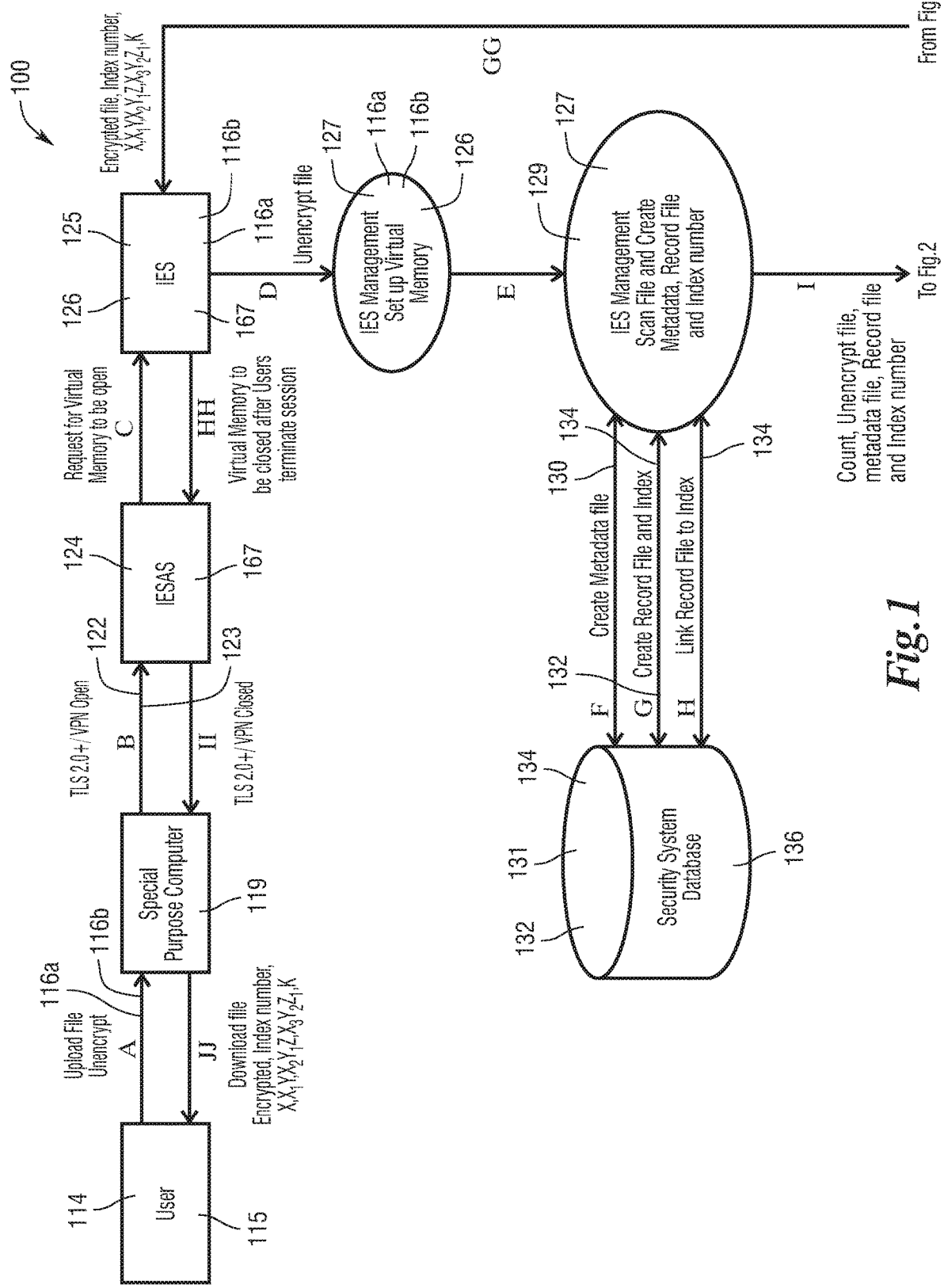

Computers now in use have technical problem that remain unresolved. This is based on the fact that the backbone of the Internet communication is cryptography. One technical problem associated with computer communication is that the encryption of files/data is subject to being accessed by unauthorized third parties once algorithms protecting the files/data have failed.

What is also troublesome is that once the unauthorized third party has figured out how to access one file/data as it is being sent, for example over the Internet, or at rest by accessing access to a database, USB, cloud-base or network-based storage devices, the unauthorized third-party user then can access every file/data being sent and received over the Internet. The unauthorized third parties can then gain access to all the data and the rest of the files in the storage devices and databases, because the security systems in place for protecting these files/data are no longer cryptographically valid.

This technical problem has yet to be resolved as proven by the fact that computers and data are being accessed by unauthorized uses. This is sometimes referred to as the computers are being "hacked" by unauthorized uses. The scope of this problem is enormous given that governmental, company and personal computers have all been hacked by unauthorized users. Currently, computers are unable toward off such attacks because they lack the technology toward off such attacks, and there is no technical solution to improve the ability of computers toward off such attacks.

Thus, what is needed is a technical solution to the technical problem of computers and computer transmissions being hacked by unauthorized third parties.

SUMMARY

There is provided a security system and an associated method for preventing unauthorized uses from gaining access to transmission of data and files. The technical problems associated with preventing unauthorized users from accessing such data and files is addressed by a technical solution that greatly improves the ability of a special purpose computer ward off such attacks. The special purpose computer runs individualized encryption software that encrypts and decrypts data and files in a way such that ability of the special purpose computer to protect against such unauthorized access is greatly enhanced as compared to present methods computers use forwarding off such attacks. As will be described presently, the technical solution provided for herein makes is almost impossible for the transmission of data and files to be accessed by unauthorized users because the individualized encryption software constructs two and three dimensional structures and makes use of a secret key when the data or files are sent to a recipient by a special purpose user computer, and the recipient has a recipient special purpose computer, and the recipient has to enter data values and the key values to open and gain access to the data or file sent by the special purpose user computer. This technical solution to the technical problem of unauthorized access to data and file transmission provides the special purpose computer with greatly enhanced capability to send encrypted data and files that cannot be hacked, but rather can only be received and opened by the recipient.

BRIEF DESCRIPTION OF THE DRAWING FIGURES

Figure 2:
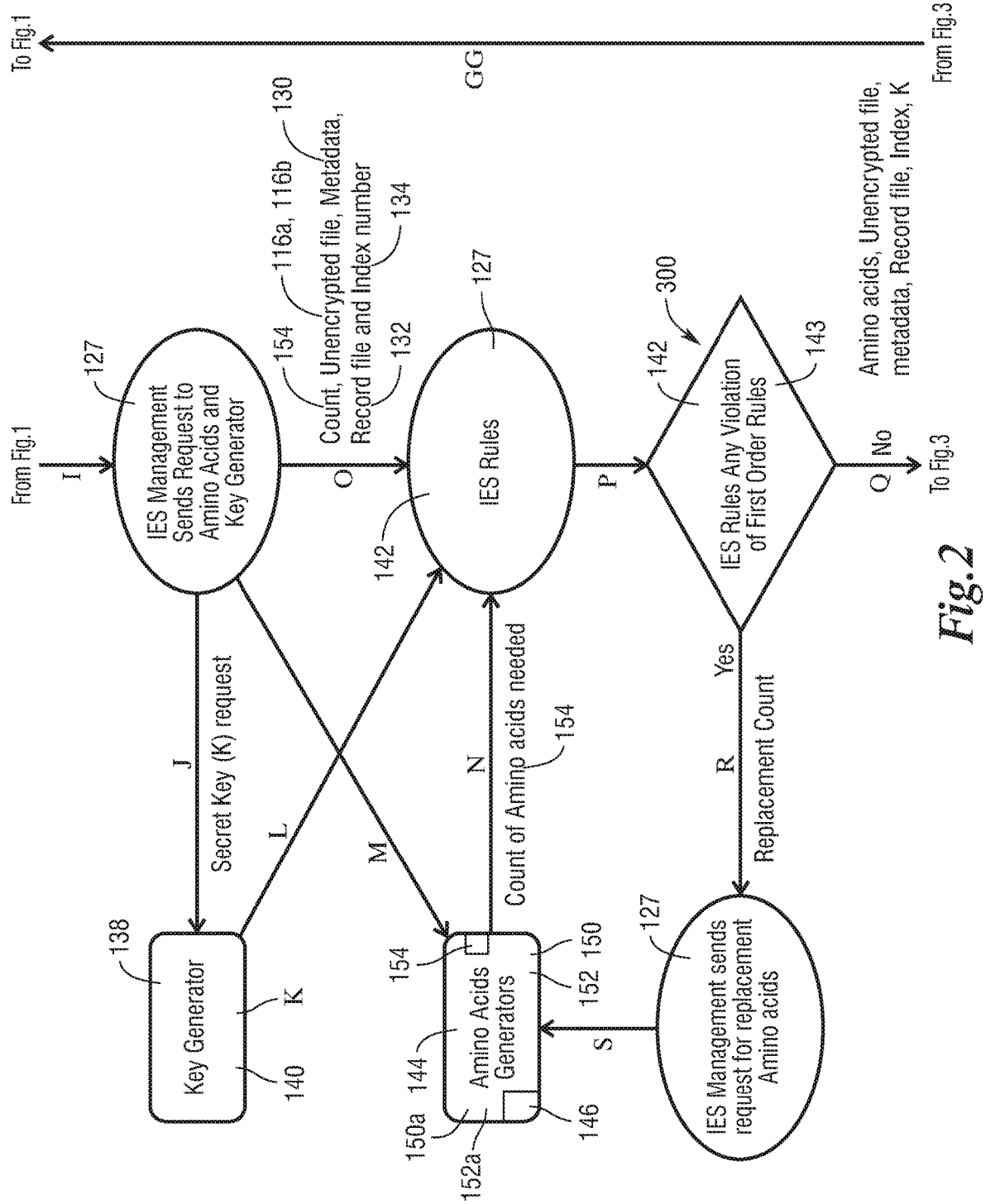
Figure 3:
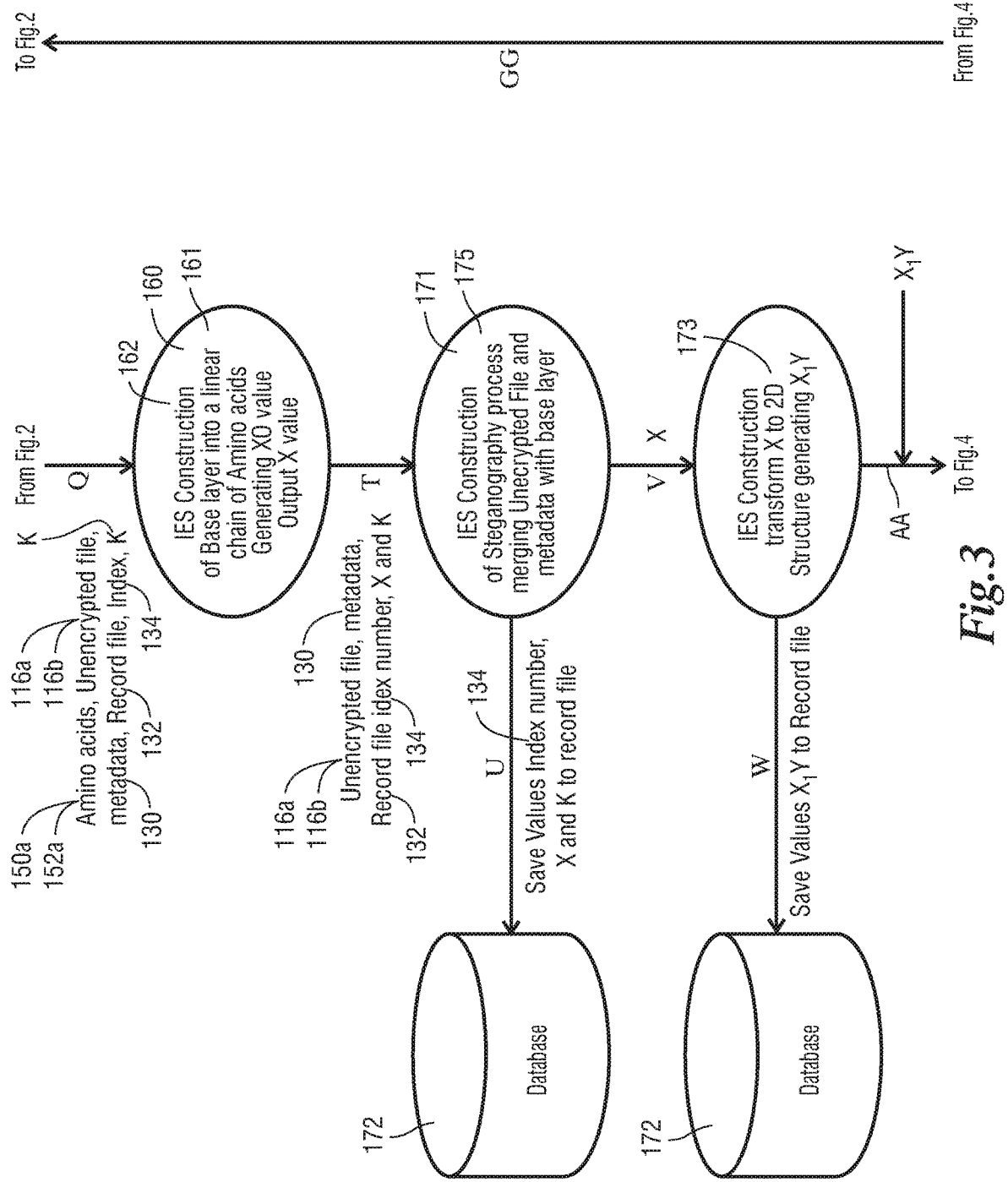
Figure 4:
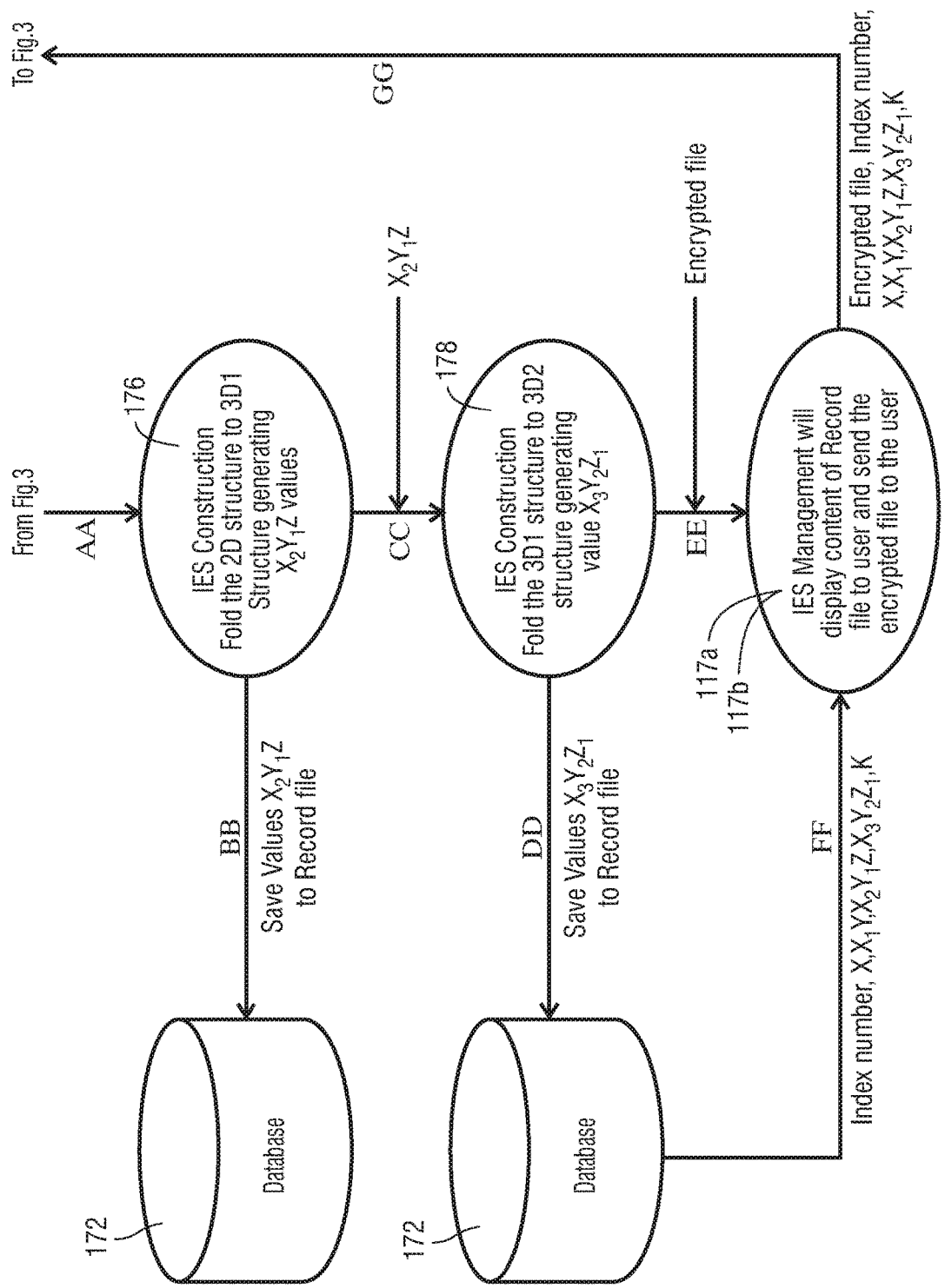
Figure 5:
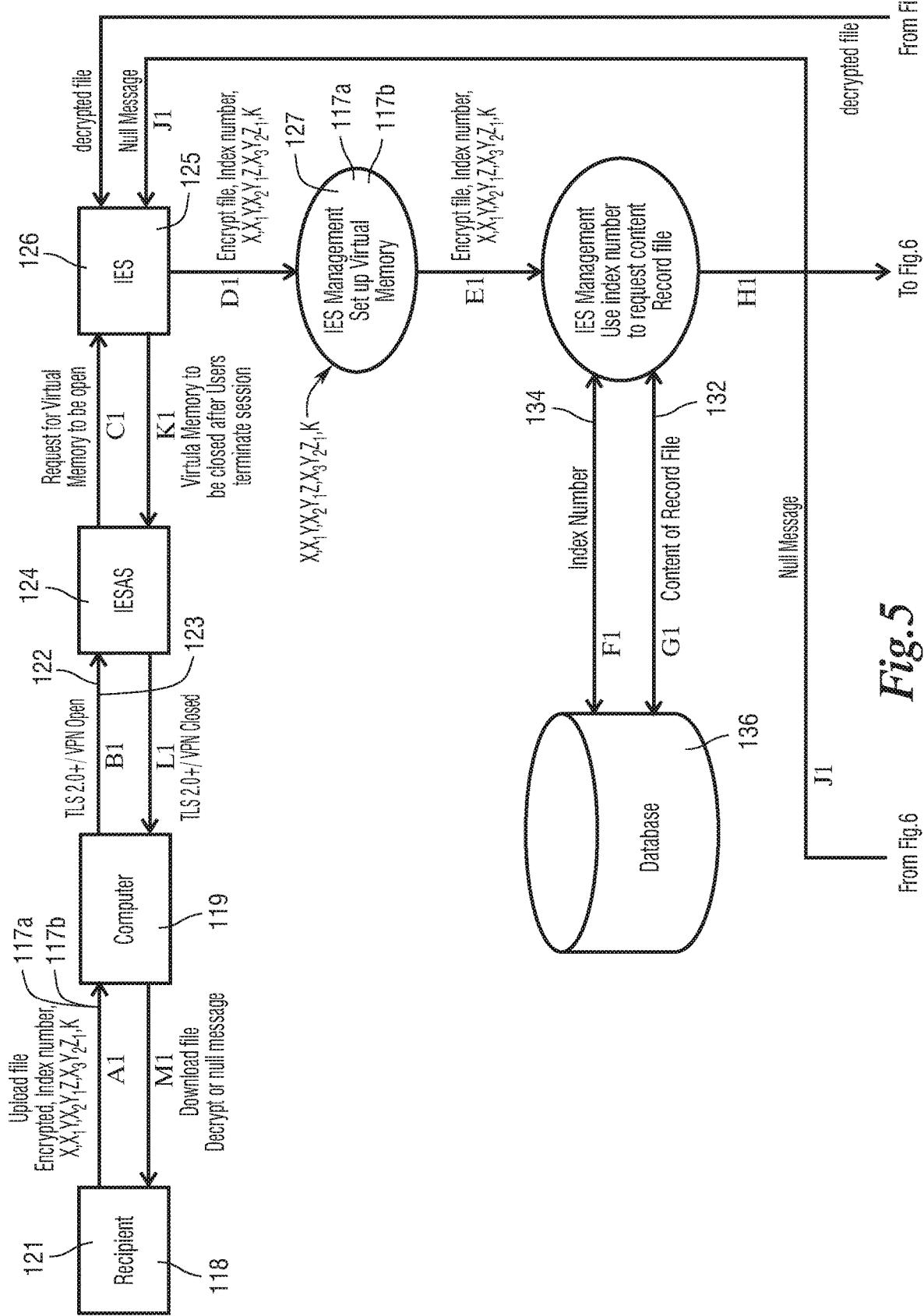
Figure 6:
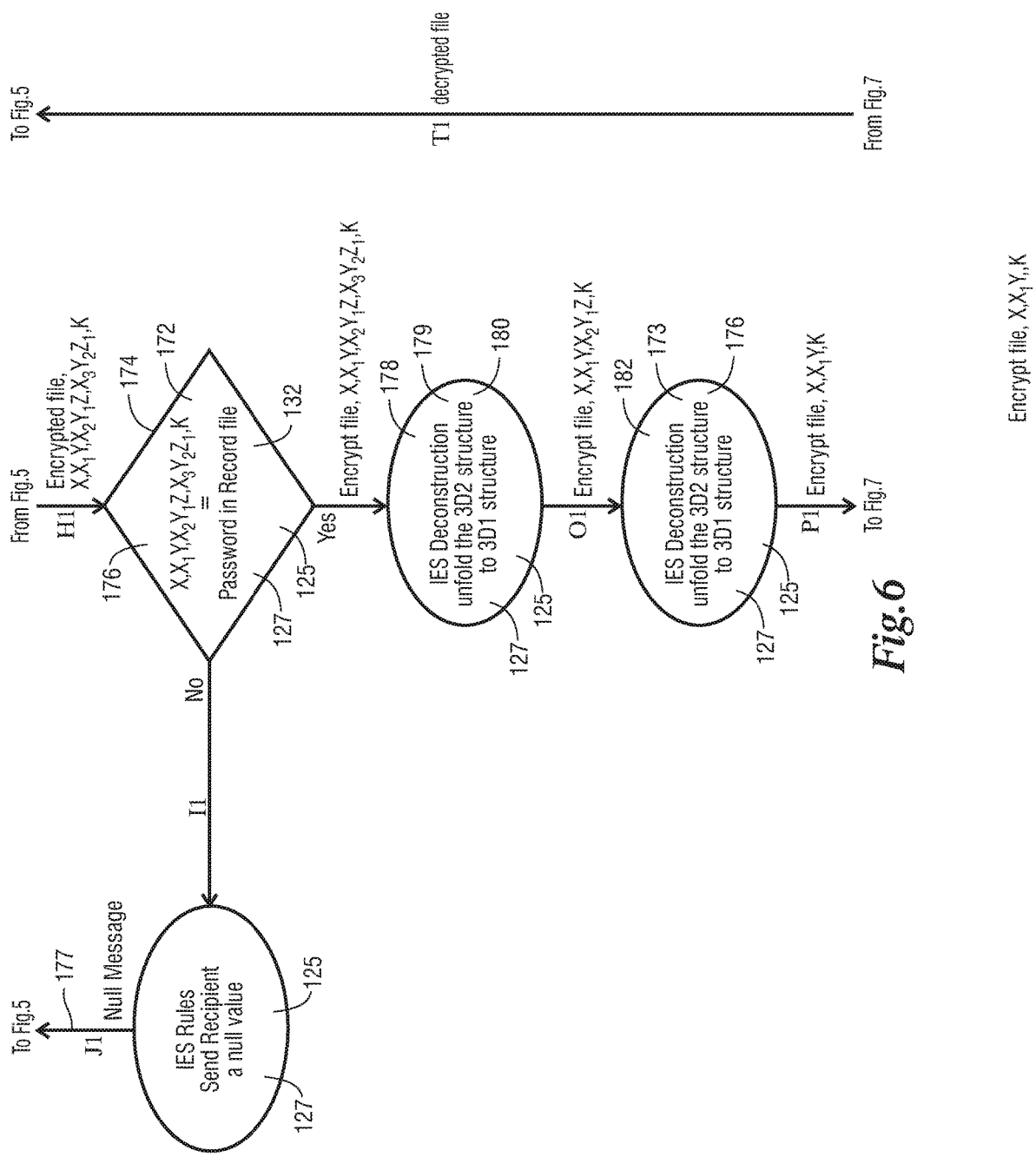

FIG. 1 is a flowchart depicting a portion of the encryption process for sending data and files.
FIG. 2 is a continuation of the flowchart shown in FIG. 1.
FIG. 3 is a continuation of the flowchart shown in FIG. 2.
FIG. 4 is a continuation of the flowchart shown in FIG. 3
FIG. 5 is a flow chart depicting a portion of the decryption process when data and files are decrypted.
FIG. 6 is a continuation of the flowchart shown in FIG. 4.
FIG. 7 is a continuation of the flowchart shown in FIG. 5

DESCRIPTION

For a better understanding of the description and claims that follow the following list is provided.

Biomimicry—Biomimicry is the design and production of materials, structures, and systems that are modeled on biological entities and processes.

Amino acids—Amino acids are naturally building blocks for creating a unique algorithm and are capable of joining together.

Each amino acid has own ability to bend, twist, and fold. Thus, the amino acids have the ability to fold into various two or three-dimensional coordinates (X, Y) or (X, Y, Z).

Each amino acid has own mathematical characteristics, and amino acids will bend, twist, and fold is depended on which amino acids it is joined to. There are 200 natural amino acids that have been found nature, but more natural amino acids may be found in nature as time progresses.

Synthetic Amino Acids—Unnatural amino acids are non-proteinogenic amino acids that either occur naturally or are chemically synthesized. There are around 10,500 synthetic amino acids and everyday new ones are being created. Whether utilized as building blocks, conformational constraints, molecular scaffolds or pharmacologically active products, unnatural amino acids represent a nearly infinite array of diverse structural elements for the development of new leads in peptidic and non-peptidic compounds. Due to their seemingly unlimited structural diversity and functional versatility, they are widely used as chiral building blocks and molecular scaffolds in constructing combinatorial. Synthetic amino acids are well known to those having skill in the art. Examples of these synthetic amino acids can be found at: libraries.http://www.sigmaaldrich.com/chemistry/chemistry-products.html?TablePage=16274965.

Present Uses of Amino Acids and Applicable for Purposes Herein

Amino acids have been used to solve over 200 puzzles for about ten years already. The online video game Foldit (https://fold.it/portal/) solve puzzle about protein folding. It is part of an experimental research project developed by the University of Washington, Center for Game Science, in collaboration with the University of Washington Department of Biochemistry. Foldit runs on Window (7,8,10), Mac (10.7 or Later) and Linux (64 bit). As will be described presently, the individualized encryption software 125 utilizes amino acids (aka protein folding) to encrypt and decrypt a file that will be able to run on the same systems Window, Mac and Linux. The central processing unit (hereinafter referred to as CPU) requirements are the same since the underlying folding techniques are the same. See the minimum CPU requirements below:

Windows 10, 8, 7
  Processor: 1 gigahertz (GHz) or faster.
Mac OSX 10.7 or later
  Intel Core 2 Duo, Core i3, Core i5, Core i7, or Xeon processor
Linux 64 bit
  32-bit Intel® Pentium® 4 or compatible processor running at 2 GHz or greater.
There are over 169 citations covering the Foldit game, here are some example:
https://www.nature.com/articles/nature09304
https://www.scientificamerican.com/article/foldit-gamers-solve-riddle/
https://www.ncbi.nlm.nih.gov/pmc/articles/PMC3645561/
Protein Structure—A string of amino acids is called a protein structure. There are commercially available software programs that have algorithms used in connection with computational modeling analysis of protein structures. An example of one commercially available by license is called Rosetta™ software. This software can be licensed from the University of Washington, located in Seattle, Wash., United States of America and can be found at https://www.rosettacommons.org/home and at the website license@uw.edu.
Building Blocks—Building blocks can be anything that has similar characteristics/attributes of amino acids. This means the blocks have the ability to join together, bend, twist and fold into two-dimensional (hereinafter referred to as 2D) and three-dimensional (hereinafter referred to as 3D) coordinates.
Brute Force Attack—This means an attacker (or hacker) submitting many passwords or phrases as possible with the hope of eventually guessing the correct password or phrase. The attacker systematically checks all possible passwords and phrases until the correct one is found. This is known as an exhaustive key search.

Computers now in use have technical problem that remain unresolved. This is based on the fact that the backbone of the Internet communication is cryptography. One technical problem associated with computer communication is that the encryption of files/data is subject to being accessed by unauthorized third parties once algorithms protecting the files/data have failed. Another technical problem is the that the encryption processes now in use take two seconds or more to encrypt the files/date and this is too slow.

What is also troublesome is that once the unauthorized third party has figured out how to access one file/data as it is being sent, for example over the Internet, or at rest by accessing access to a database, USB, cloud-base or network-based storage devices, the unauthorized third-party user then can access every file/data being sent and received over the Internet. The unauthorized third parties can then gain access to all the data and the rest of the files in the storage devices and databases, because the security systems in place for protecting these files/data are no longer cryptographically valid.

The technical solution provided for herein improves the security provided for by the computer and enhances the security provided for by the computer when data/files are sent, received or accessed from secure storage such as by way of a network, universal serial bus (USB), the cloud or a database.

For example, the advanced encryption cipher (hereinafter referred to as AES) has been selected by governments, companies and even individuals to protect classified information and is implemented in software and hardware throughout the world to encrypt sensitive data. AES is a symmetric block cipher that is a method of encrypting text to produce ciphertext in which a cryptographic key and algorithm are applied to a block of data. There are block ciphers including AES-128, AES-192, and AES-256 that encrypt and decrypt data by way of cryptographic keys. AES-256 encryption and its use and operation are well known to those having ordinary skill in the art and therefore are not described in greater detail herein. The AES-256 symmetric key algorithm is computationally secure against third party computer attacks with a relative strength of $10^{77}$, meaning this many computational attempts would have to made to gain access to an encrypted file or data. This is a large number and is generally consider a reliable way of encrypting a file or data because of the great number of calculations that would have to be conducted to access the encrypted file or data. Governments, corporations and individuals all use AES-256 symmetric key algorithm for purposes of security. However, AES-256 is not impenetrable and has been known to be insufficient for securing files and data. In addition, there is a time lag when encrypting files and data with AES-256 symmetric key algorithm that is over a second or more. Thus, there exists a technical problem with computers because they are allowing unauthorized users to gain access to files and data, but at the same time have no way to prevent the unauthorized users from gaining access to data and files. As a result of this technical problem there have been and there will continue to be security breaches wherein unauthorized third parties gain access to files and data causing financial harm, loss of confidence in e-commerce, and harm to the public.

The technical problem mentioned above is resolved by the technical solution described herein. The technical solution improves the security provided by computers and enhances the security proved by the computer when files and data are sent and received. The invention provides a technical solution to this technical problem by increasing the relative strength against a third party brute force attack of strength of $10^{77}$ to relative strength against a third party brute force attack strength of $10^{100}$, meaning this many attempts would have to made to gain access to an encrypted file or data making it virtually impossible the encrypted file to be opened by unauthorized third parties. The technical solution also solves the issues associated with AES-256 algorithm lag time. The technical solution provided for herein decreases the time to encrypt and decrypt files/date to a millisecond as compared to seconds required for the AES-256. This is accomplished because the present invention of the nature of the security provided for herein only needs to be performed once for encryption and not fourteen (14) rounds as required for AES-256. In addition, the technical solution does not put other files/data from be accessed by the unauthorized user, even if the unauthorized user is able to break the encryption and gains access to one file or piece of data. That is, the technical solution prevents unauthorized users from gaining access to other files/data, even if the unauthorized somehow and manage to break the encryption and gain access to one file/data. This is quite a technical solution that greatly enhances the performance and operation of the computer in view of the fact that in other computer security systems once the unauthorized user has broken encryption and gain access to one file such unauthorized user has access to all the files/data. For example, if a computer experiences an attack from third parties, the third parties can gain access to any and all computer files/data, and when files/data are sent or received. The technical solution provided herein, even if unauthorized users have broken the encryption and gain access to one file, the remaining files/data are not accessible, meaning the computer is equipped to prevent mass scale security breaches, because it is virtually impossible for there to be a mass scale security breach since each file/data has its own unique encryption algorithms.

Turning now to FIG. 1, shown therein is another embodiment that has a security system 100 that overcomes and solves technical problems mentioned above, such that unencrypted files/data 116a, 116b can be sent and opened with little to almost no risk the file/data 116a, 116b will be accessed by an unauthorized third party. For purposes of this description and the claims that follow, the terms file 116a and data 116b are used interchangeably. There is a user 114 having a special purpose user computer 115 capable sending data/files 116a/116b to a recipient 118 having a recipient special purpose computer 121. The security system 100 includes a special purpose computer 119, and the user 114 uploads unencrypted file/data 116a, 116b from the special purpose user computer 115 to the special purpose computer 119 as indicated by the arrow designated A. The security system 100 also includes an individualized encryption software applicant server 124 (hereinafter referred to as IESAS 124) that is operatively associated with the special purpose computer 119 or is wired to the special purpose computer 119. The communication from the special purpose computer 119 to the IESAS 124 is by way of transport security layer 2.0+ (hereafter referred to as TSL 2.0+) and indicated by reference numeral 123 and the arrow designated B, or by virtual private network 122 (hereinafter referred to as VPN 122) also indicated by the arrow designated B. As shown, the IESAS 124 of the security system 100 has a temporary virtual memory partition component 126 so that so the files/data 116a, 116b can be transferred to the temporary virtual memory partition component 126, and the IESAS 124 sends a request to the temporary virtual memory partition component 126 to open as indicated by the arrow designated C. The temporary virtual memory partition component 126 is temporary and will be terminate after is has been used, and this safeguards and ensures that there is no files/data 116a, 116b remaining in the temporary virtual memory partition component 126 after it has been used to store files/data 116a, 116b. The IESAS 124 of the security system 100 also includes individualized encryption software 125 (hereinafter referred to as IES 125) that is preprogrammed to perform a series of steps as will be described presently. The IESAS 124 does all encryption and decryption of the files/data 116a, 116b and this one of the technical solutions provided for herein, because this eliminates third party side channel attacks, in other words, third parties cannot analyze the IESAS 124 and cannot analyze the IES 125.

FIG. 1 also shows the IES 125 includes individualized management software 127 that is programmed to generate and set up the temporary virtual memory partition component 126 as indicated by the arrow designated D, and the unencrypted files/data 116a, 116b are stored in the temporary virtual memory partition component 126.

As indicated by the arrow designated E, the individualized management software 127 scans the unencrypted files/data 116a, 116b and creates metadata 130 and a metadata file 131; and creates a record file 132 and an associated index number 134. The security system 100 also includes a security system database 136 for storing the metadata file 131, the record file 132 and the index number 134. The arrow designated F shows the exchanges made to and from the security system database 136 and the metadata file 131 and the individualized management software 127. The arrow designated G indicates the exchanges made to and from the security system database 136 and the record file 132 and index number 134 and the individualized management software 127 to create the record file 132 and the index number 134. And, the arrow designated H indicates the exchanges made to and from the security system database 136 and the and the individualized management software 127 to link the record file 132 and index number 134. In addition, the individualized management software 127 determines how many natural and synthetic amino acids 150, 152 are required for the encryption process as will be described in greater detail presently.

After this is completed and as indicated by the arrow designated I, that comes from FIG. 1 and continues to FIG. 2, the individualized management software 127 moves to the next step as shown in FIG. 2.

As shown, the security system 100 and the individualized management software 127 further includes secret key generator program 138 that generates a secret key 140 that is designated herein by the letter K and K has a value, and the K value is a numeral, and in other embodiments may be alphanumeric. The individualized management software 127 makes a request to the secret key generator program 138 as indicated by the arrow designated J, and the secret key generator program 138 outputs the secret key K, that may be embodied as, for example numbers, letters, or symbols, to an individualized encryption software rules program 142 of the individualized management software 127, and as indicated by the arrow designated L.

The security system 100 further includes an amino acids generator program 144 that randomly selects natural and synthetic amino acids 150, 152 from a secure amino acid database 146. The individualized management software 127 makes a request to the a secure amino acids generator program 144 as indicated by the letter M that has access to the secure amino acid database 146. The secure amino acid database 146 stores 10,700 natural amino acids 150 and synthetic amino acids 152, that is it stores natural amino acids data 150a and synthetic amino acids data 152a. In other embodiments there may be more or less that 10,700 natural and synthetic amino acids 150, 152, and in other embodiments there may be only natural amino acids 150 or only synthetic amino acids 152. Each of the natural and synthetic amino acids 150, 152 has is own ability to bend, twist, and fold. This ability to fold and twist into two-dimensional (2D) coordinates (X, Y) or three-dimensional (3D) coordinates (X, Y, Z) means that each of the natural and synthetic amino acids 150, 152 has its own mathematical characteristics and associated three dimensional data characteristics. Due to the very nature of the natural and synthetic amino acids 150, 152 they bend, twist, and fold according to which of the natural and synthetic amino acids 150, 152 they are joined with. The mathematical characteristics are given to each of the natural and synthetic amino acids 150, 152 are known before they are entered into the secure amino acids database generator 144.

As will be described presently, the secure amino acids database 146 is used, in part, to solve the technical problem of creating unique algorithms for each unencrypted file/data 116a, 116b used in a transaction. In contrast, presently when a symmetry algorithm is broken or accessed every file/data that made use of that symmetry algorithm is at risk of being accessed by an unauthorized user. The present invention provides a technical solution to this technical problem in that each time files/data 116a, 116b are transferred each file/data 116a, 116b has its own unique algorithm associated with that file/data 116a, 116b. Thus, only one file/data 116a, 116b is at risk of being accessed by unauthorized users. For example, with this technical solution, the IESAS 124 can encrypt 20 million files/data and there would be 20 million different algorithms. Thus, if one of the algorithms is accessed by an unauthorized user and accessed is gained to one file/data 116a, 116b, then the other 19,999,999 files/data 116a, 116b would be safe and not accessed. The technical solution provided by the IESAS 124 greatly improves its ability to provide security and improves the function and efficiency of the special purpose computer 119 running the individualized encryption software 125 in overcoming security problems. Thus, security related to transactions of files/data 116a, 116b is improved because of the improved operation and functionality provided by the IESAS 124 as compared to other security methods and techniques.

Also shown in FIG. 2, the secure amino acids generator program 144 provides an amino acid count number 154 of the number of natural and synthetic amino acids 150, 152 that are needed for encrypting a transmission of an unencrypted file/data 116a, 116b. The individualized management software 127 includes individualized encryption software rules program 142. The amino acid generator program 144 sends the amino acid count number 154 of the natural amino acids data 150a and synthetic amino acids data 152a (of the natural and synthetic amino acids 150, 152) that are needed for the transaction and transmits the count 154 to the individualized encryption software rules program 142 as indicated by the arrow designated N along with the amino acid count number 154 and the natural amino acids data 150a and synthetic amino acids data 152a to be used for encrypting the file/data 116a, 116b.

However, before using the structure of the natural and synthetic amino acids provided for in the natural amino acids data 150a and synthetic amino acids data 152a (for purposes of encrypting the file/data 116a, 116b and as will be described presently), the individualized encryption software 125 has individualized encryption software rules program 142 that are followed to carry out the steps of encryption, as indicated by the arrow designated O.

Next, as indicated by the arrow designated P, the individualized encryption software rules program 142 determines if the process described above violated any first order rules 143 of the individualized encryption software rules program 142, as indicated by decision box designated 300 in FIG. 2. That is, the individualized encryption software rules program 142 is programmed to follow what are called first order rules 143. Each time that the natural and synthetic amino acids 150, 152 are randomly selected from the secure amino acid database 146 the individualized encryption software rules program 142 processes the associated natural amino acids data 150a and synthetic amino acids data 152a to determine if any first order rules 143 are violated by the selection of these natural and synthetic amino acids 150, 152.

The first order rules 143 of the individualized encryption software rules program 142 are as follows:

a)—there is no duplication of natural and synthetic amino acids 150, 152 (natural amino acids data 150a and synthetic amino acids data 152a) in what is called an amino acid base layer 160; and, b)—the total number of natural and synthetic amino acids 150, 152 (natural amino acids data 150a and synthetic amino acids data 152a) are made up ⅓ natural amino acids 150 and ⅔ synthetic amino acids 152.

In other embodiments the these amounts can be varied, for example, the number of natural amino acids 150 is forty percent and the number of synthetic amino acids 152 is sixty percent. Thus, the percentages of natural and synthetic amino acids 150, 152 and the data associated with these may be varied in other embodiments.

If these first order rules 143 are not violated, or once they are no longer violated, then the process continues as shown by the arrow designate Q. But, if this first order rule 143 is violated, then, as indicated by the arrow designated R, then the individualized management software 127 repeats this step as indicated by the arrow designated S and request another natural or synthetic amino acid 150, 152 as shown by arrows N and P. This process repeats until the first order rule 143 is no longer violated.

Then, as shown in FIG. 3, which continues from FIG. 2 and as indicated by the arrow designated Q, the natural and synthetic amino acids data 150a, 152a, the unencrypted file/data 116a, 116b, the metadata file 131, the record file 132, the index number 134 and K value are shown. The IES 125 constructs the natural and synthetic amino acids 150, 152 into the amino acid base layer 160, and the amino acid base layer 160 is an amino acid linear chain 161 constructed from the natural and synthetic amino acid data 150a, 152a. The amino acid base layer 160 has an XO value. The XO value is the length of the linear amino acid linear chain 161 without any data/file 116a, 116b attached to it. It is noted that the natural and synthetic amino acids 150, 152 have carboxyl groups that bond to another amino acid group to a given length, such that the amino acid base layer 160 has a length designated XO. In one embodiment eighty (80) natural and synthetic amino acids 150, 152 are utilized and the natural and synthetic amino acid data 150a, 152a for these are known. In other embodiments there may be more or less than eighty (80) natural and synthetic amino acids 150, 152 utilized. In other embodiments only natural amino acids 150 or only synthetic amino acids 152 are used.

As will be described presently, when the file/data 116a, 116b is merged into linear amino acid linear chain 161 with steganographic coding 171 an X value is generated as shown in FIG. 3. The X value is the output of the merging of the amino chain 161 and the file/data 116a, 116b when a steganographic processes is used.

As shown by the arrows designated T in FIG. 3, the unencrypted file/data 116a, 116b, the metadata file 130, the record file 132, the index number 134, the X and K values are processed by the individualized management software 127. Then, steganography is applied merging the unencrypted file/data 116a, 116b and the metadata 130 and the amino acid base layer 160. Steganography is the practice of concealing a files, data, messages, images, or video within another file, message, image, or video. In digital steganography, electronic communications may include steganographic coding inside of a transport layer. Media files are well suited for steganographic transmissions because of their large size. For example, a sender might start with an innocuous image file and adjust the color of every hundredth pixel to correspond to a letter in the alphabet. The change is so subtle that someone who is not specifically looking for it is unlikely to notice the change. Steganography is directed to concealing the fact that the file/data 116a, 116b, the metadata file 131, the record file 132, the index number 134, and K value are being sent, as well as concealing the contents of the file/data 116a, 116b.

The individualized encryption software 125 has steganography programming 167 that allows for steganographic coding 171. The steganography coding 171 provides for a steganographic layer 175 that merges with the unencrypted file/data 116a, 116b and the metadata file 131, and then merges this with the amino acid base layer 160. This produces an X value that is numeric. This is, XO denotes a newly formed amino acids chain and when the file/data 116a, 116b is merged into the XO chain using steganography code (layer 175) it forms the previously mentioned X value.

As shown by the arrow designated U the index number 134, the X value, and K values are saved in a record file database 172.

As shown by the arrow designated V the individualized encryption software 125 processes the X value described above into a two dimensional structure (indicated by 2D and reference numeral 173 in FIG. 3), and generates $X_1Y$ numeric coordinate values that are stored in the record file database 172 as indicated by the arrow designated W.

As shown by the arrow designated AA shown in FIG. 3 and continuing onto FIG. 4, the individualized encryption software 125 folds the two dimensional structure 173 into a first three dimensional structure (a first 3D1 structure) indicated by reference numeral 176 and generates $X_2Y_1 Z$ numeric coordinate values, and the $X_2Y_1 Z$ numeric coordinate values are saved in the record file database 172 as indicated by the arrow designated BB.

As shown by the arrow designated CC the individualized encryption software 125 folds the first three dimensional structure 176 into a second three dimensional structure (a 3D2 structure) indicated by reference numeral 178 and generates $X_3Y_2 Z_1$ numeric coordinate values, and the $X_3Y_2Z_1$ numeric coordinate values are saved in the record file database 172 as indicated by the arrow designated DD. The individualized management software 127 has the thus encrypted the file/data 116a, 116b into an encrypted file/data 117a, 117b that is encrypted by the index number 134 and the X, $X_1Y$, $X_2Y_1 Z$, $X_3Y_2 Z_1$, numeric coordinate values and the K numeric value as indicated by the arrow designated FF.

As an example, the numeric coordinate values may be as follows, with the understanding these values change every time data/file 116a, 116b are encrypted:

X=221

Two dimensional structure 173 coordinates:

$X_1$=23.34

Y=−9

First three dimensional structure 176 coordinates:

$X_2$, $Y_1$, Z=66.3, 300, 17.05

Second three dimensional structure 178 coordinates:

$X_3Y_2Z_1$=107.3, −58.11, 45

And the K value may be 76.

It is to be understood that in another embodiment the individualized encryption software 125 can fold the a second three dimensional structure (a 3D2 structure) 178 again into a third three dimensional structure (a 3D3 structure) providing additional numeric coordinate values, and that can be folded again providing more numeric coordinates, or may only have the first three dimensional structure 176 or may just have the two dimensional structure 173.

The individualized management software 127 will display the content of the record file 132 to the user 114 and send the encrypted file/data 117a, 117b to the user 114 as indicated by the arrow designated GG. Arrow GG leads back to FIG. 3 on page 3 of the drawing figures, and then to FIG. 2 and then to FIG. 1.

FIG. 3 shows the index number 134 and X, $X_1Y$, $X_2Y_1 Z$, $X_3Y_2 Z_1$, numeric coordinate values and K numeric values are transmitted back to the individualized encryption software 125 such that the encrypted file/data 117a, 117b and as indicated by the arrow designated HH, and then to the individualized encryption software applicant server 124 as indicated by the arrow designated II, and then to the special purpose computer 119, and then downloaded to the special purpose user computer 115 as indicated by the arrow designated JJ that the user 114 can access the encrypted file/data 117a, 117b and send it to a recipient special purpose computer 121 as will be described presently.

It is to be understood that in another embodiment the individualized encryption software 125 processes the X value to the two dimensional structure 173 and generates an $X_1Y$ numeric values that are stored in the record file database 172 as indicated by the arrow designated W. In this embodiment there is no additional folding of the two dimensional structure 173. In another embodiment the second three dimensional structure 178 is absent.

Sending and Opening the Encrypted File by Recipient

As shown in FIG. 5, the recipient 118 of the encrypted file/data 117a, 117b will need to decrypt these. The recipient 118 has a special purpose recipient computer 121 that uploads the encrypted file/data 117a, 117b, index number 134, and the X, $X_1Y$, $X_2Y_1 Z$, $X_3Y_2 Z_1$, numeric values and the K value to the special purpose computer 119 as indicated by the arrow designated A1. The individualized encryption software applicant server 124 (IESAS 124) is in communication or may be wired to the special purpose computer 119. The communication from the special purpose computer 119 to the IESAS 124 is by way of transport security layer 2.0+ (hereafter referred to as TSL 2.0+) and indicated by reference numeral 122 and the arrow designated B1, or by virtual private network 123 (hereinafter referred to as VPN 123) also indicated by the arrow designated B1.

IESAS 124 sends a request to the temporary virtual memory partition component 126 to open as indicated by the arrow designated C1. The virtual memory partition component 126 is temporary and will be terminate after is has been used, and this safeguards and ensures that there are no files/data 116a, 116b, encrypted or not encrypted, remaining in the virtual memory partition component 126 after it has been used to store files/data 116a, 116b. The IESAS 124 of the security system 100 also includes individualized encryption software 125 (IES 125) that is preprogrammed to perform a series of steps as will be described presently.

The individualized management software 127 sets up the virtual memory partition component 126, and as indicated by the arrow designated D1, the encrypted files/data 117a, 117b, the index number 134 and the X, $X_1Y$, $X_2Y_1 Z$, $X_3Y_2 Z_1$, numeric coordinate values and K value described above are stored in the virtual memory partition component 126 for processing by the individualized management software 127.

As indicated by the arrow designated E1, the individualized management software 127 sends the index number 134 to the security system database 136 as indicated by the arrow designated F1 and requests the content of the record file 132, and the content of the record file 132 is sent to the individualize management software 127 as indicated by the arrow designated G1.

As indicated by the arrow designated H1 in FIG. 5 and continuing onto FIG. 6, the encrypted file/data 117a, 117b, and the X, $X_1Y$, $X_2Y_1 Z$, $X_3Y_2 Z_1$ numeric coordinate values and K value in the record file 132 are processed by the individualized management software 127, as indicated by the decision box 174. The index number 134, and the X, $X_1Y$, $X_2Y_1 Z$, $X_3Y_2 Z_1$, numeric coordinate values and K value function as a password 174. If the recipient 118 enters the wrong values for these inputs, then, as shown by the arrow designated I1 a transmission is made to the individualized management software 127 to return a "null" message 177 or response indicated by numeral 177 and the arrow designated J1. The null message 177 is transmitted by the individualized encryption software 125, to the individualized encryption software applicant server 124 as indicated by the arrow designated K1, to the special purpose computer 119 as indicated by the arrow designated L1, and then to the recipient special purpose computer 121 as indicated by the arrow designated M1, and the recipient 118 will not be able to open the encrypted file/data 117a, 117b.

If a null message 177 is not sent, then as indicated by the arrow designated N1 the index number 134, the encrypted file/data 117a, 117b, and the X, $X_1Y$, $X_2Y_1$ Z, $X_3Y_2$ $Z_1$, numeric coordinate values and the K value are processed by the individualized encryption software 125. The second three dimensional structure $X_3Y_2$ $Z_1$ designated 3D2 and indicated by reference number 178 is unencrypted to become the first three dimensional structure 3D1 indicated by reference numeral 176 and indicated by first ring designated 180. At this step the index number 134, encrypted file/data 117a, 117b and X, $X_1Y$, $X_2Y_1$ Z, $X_3Y_2$ $Z_1$, numeric coordinate values and K become the index number 134, the encrypted file/data 117a, 117b and X, $X_1Y$, $X_2Y_1$, Z numeric coordinate values and the K value as shown.

As shown in FIG. 6, the deconstruction or un-encryption moves to the next step as indicated by the arrow designated O1 and indicated by a second ring designated 182. Here, the individualized encryption software 125 further deconstructs or un-encrypts the first three dimensional structure (3D1) indicated by reference numeral 176 into a two dimensional (2D) structure designated and indicated by reference numeral 173. At this point there is the encrypted file/data 117a, 117b, the index number 134, the and X, $X_1Y$, and K values as shown.

As shown in FIG. 7 which continues from FIG. 6, the deconstruction or un-encryption moves to the next step as indicated by the arrow designated P1. Here, the individualized encryption software 125 further deconstructs or un-encrypts the two dimensional structure 2D indicated by reference numeral 173 into an X structure that has the X value as indicated by reference numeral 189 and ring 190. After deconstruction there is left the encrypted file/data 117a, 117b, the index number 134, and the X and K values as shown.

As indicated by the arrow designated Q1, the next step the individualized encryption software 125 takes is to remove the steganography from encrypted file/data 117a, 117b as indicated by reference numeral 191 and a fifth ring 192 and verify the K value, to reveal the data/file 116a, 116b that is no longer encrypted.

Next, as indicated by the arrow designated R1 the individualized management software 127 that is part of the individualized encryption software 125 sends the unencrypted file/data 116a, 116b to the recipient special purpose computer 121 as indicate by a sixth ring 194. The individualized encryption software 125 also sends the metadata file 131 and metadata 130 to the security system database 136 as indicated by the arrow designated S1.

Next and as indicated by the arrow designated T1, the decrypted file/data 116a, 116b is sent back to the individualized encryption software applicant server 124 as indicated by the arrow designated K1, then to the special purpose computer 119 as indicated by the arrow designated L1, and then to the recipient special purpose computer 121. The recipient 118 can then open the file/data 116a, 116b that has been decrypted and can access the file/data 116a, 116b on his or her recipient special purpose computer 121 as indicated by the arrow designated M1. To open the file/data 116a, 116b the recipient now only needs to enter the proper index number 134, the proper X, $X_1Y$, $X_2Y_1$ Z, $X_3Y_2$ $Z_1$, numeric coordinate values and the proper K value.

Thus, the technical problems associated with computers receiving and sending secured transmissions of file(s)/data 116a, 116b is enhanced. This means the functioning of the special purpose computer 119 is itself is greatly technically enhanced. The technical solution to the technical problems described above make the sending and receiving of file/data 116a, 116b greatly improved and the functioning is also greatly enhanced because it can provide for enhanced security at a speed that superior to as compared to other methods used in computer security. In addition, the functioning and operation of the special purpose computer 119 also improved and superior to other security methods and systems because is provides for great security in a matter of a millisecond, as compared with current security systems that take seconds for secure transactions. Thus, the present security system 100 provides for a special purpose user computer 115 that uses the individualized encryption software applicant server 125 running individualized encryption software to provide the technical solution to these technical problems.

Other Building Blocks

It is to be understood that other embodiments the natural and synthetic amino acids 150, 152 can be replaced with other materials, substances, and the like that have similar characteristics/attribute of natural and synthetic amino acids 150, 152. This includes blocks that are capable of joining together, bending, twisting and fold into 2D and 3D coordinates. For example, macrocycles that are a synthetic man-made molecules that can self-fold and self-assemble. These could replace the natural and synthetic amino acids 150, 152, and the appended claims are intended to cover such variations.

It will be appreciated by those skilled in the art that while the security system 100 and method have been described in detail herein, the invention is not necessarily so limited and other examples, embodiments, uses, modifications, and departures from the embodiments, examples, uses, and modifications may be made without departing from the security system 100 and method and all such embodiments are intended to be within the scope and spirit of the appended claims.

What is claimed:

1. A security system for use in connection with improving the security of a file sent by a user having a special purpose user computer to a recipient having a recipient special purpose computer, the security system comprising:
    an individualized encryption software application server;
    the special purpose user computer that is in communication with the individualized encryption software application server by way of transport layer security, such that the file to be sent from the special purpose user computer to the recipient special purpose computer;
    the individualized encryption software application server has individualized encryption software that includes individualized management software;
    the individualized management software scans the file that is unencrypted and generates metadata, and a metadata file, a record file and an associated index number;
    a security system database for storing the metadata file, the record file and the index number;
    the individualized management software scans the file and determines the number of natural and synthetic amino acids required to encode an amino acid base layer, and the amino acid base layer is in the form of an amino acid linear chain made of the natural and synthetic amino acids and has a length designated XO;

the individualized management software includes a secure amino acids generator program and there is an amino acid database for storing natural amino acids and synthetic amino acids data, and the individualized management software sends a request to the secure amino acids generator program that randomly selects natural and synthetic amino acids from the amino acids database, and the secure amino acid database generator generates the mathematical characteristics of the natural and synthetic amino acids;

the individualized management software includes a steganography program and steganography is applied to the file, and the individualized management software merges the file with the linear amino acid linear chain having a length XO and outputs an X value;

the individualized management software includes a secret key generator for generating a secret key having a K value;

the individualized encryption software processes the X value into a two dimensional structure having $X_1$ and Y numeric coordinate values that are saved in a record file database;

the individualized encryption software mathematically folds the two dimensional structure into a first three dimensional structure and generates $X_2Y_1Z$ numeric coordinate values, and the $X_2Y_1Z$ numeric coordinate values are saved in the record file database;

the individualized encryption software mathematically folds the first three dimensional structure into a second three dimensional structure and generates $X_3Y_2Z_1$ numeric coordinate values, and the $X_3Y_2Z_1$ numeric coordinate values are saved in the record file database;

wherein the file is encrypted with the index number, the X value, the secret key value K, the $X_1Y$ numeric coordinate values, the $X_2Y_1Z$ numeric coordinate values, and the $X_3Y_2Z_1$ numeric coordinate values and the encrypted file can be sent from the special purpose user computer to the recipient special purpose computer; and wherein the index number, the $X_1Y$ numeric coordinate values, the $X_2Y_1Z$ numeric coordinate values, and the $X_3Y_2Z_1$ numeric coordinate values and the secret key with K value function as a password such that if the recipient enters the correct values for each, then the individualized encryption software allows the file to be decrypted.

2. The security system according to claim 1 wherein the individualized management software determines an amino acid count number of the natural and synthetic amino acids that are needed for encrypting the file.

3. The security system according to claim 2 wherein the individualized management software includes an individualized encryption software rules program that is programmed to follow first order rules, and each time the natural and synthetic amino acids are randomly selected from the secure amino acid database the individualized encryption software rules program processes the natural and synthetic amino acid data to determine if any first order rules are violated by the selection of these natural and synthetic amino acids.

4. The security system according to claim 3 wherein the individualized encryption software rules program executes the first order rules such that each time the natural and synthetic amino acids are selected they are processed to determine if there is any duplication of natural and synthetic amino acids in the amino acid base layer and if there is duplication of natural and synthetic amino acids in the amino acid base layer then a new amino acid base layer is automatically generated by the individualized encryption software rules program until there is no duplication of the natural and synthetic amino acids in the amino acid base layer.

5. The security system according to claim 4 wherein the individualized encryption software rules program also selects natural and synthetic amino acids from the secure amino acid database such that the total the total number of natural and synthetic amino acids are ⅓ natural amino acids and ⅔ synthetic amino acids and if this ratio is not achieved, then the individualized encryption software rules program selects different natural and synthetic amino acids until there are ⅓ natural amino acids and ⅔ synthetic amino acids.

6. The security system according to claim 5 wherein the individualized encryption software application server has a temporary virtual memory partition component so that the file can be transferred to the virtual memory partition component, and the individualized encryption software applicant application server having the temporary virtual memory partition component opens when instructed to receive the file, and wherein the virtual memory partition component is temporary and will be terminate after it has been used so that no file remains in the virtual memory partition component after the virtual memory partition component has been used to store the file.

7. The security system according to claim 6 wherein the index number, the X, $X_1Y$, $X_2Y_1$ Z, $X_3Y_2$ $Z_1$ numeric coordinate values and the K value are sent from the special purpose user computer to the recipient special purpose computer.

8. The security system according to claim 7 wherein the recipient special purpose computer uploads the encrypted file, the index number, and the X, $X_1Y$, $X_2Y_1$ Z, $X_3Y_2$ $Z_1$, numeric values and the K value to the special purpose computer.

9. The security system according to claim 8 wherein the individualized encryption software application server sends a request to the temporary virtual memory partition component to open and the encrypted files, the index number and the X, $X_1Y$, $X_2Y_1Z$, $X_3Y_2Z_1$, numeric coordinate values and K value are stored in the virtual memory partition component.

10. The security system according to claim 9 where the individualized management software sends the index number to the security system database and requests the content of the record file and the content of the record file is sent to the individualized management software, and the encrypted file and the index number, the X, $X_1Y$, $X_2Y_1Z$, $X_3Y_2Z_1$ numeric coordinate values and K value in the record file are processed by the individualized management software.

11. The security system according to claim 10 wherein the index number, the X, $X_1Y$, $X_2Y_1Z$, $X_3Y_2Z_1$ numeric coordinate values and the K value function as a password such that if the recipient attempts to open the encrypted file with the values other than these values the recipient receives a null message and cannot open the encrypted file.

12. The security system according to claim 1 wherein the individualized encryption software decrypts the second three dimensional structure $X_3Y_2Z_1$ into numeric coordinate values.

13. The security system according to claim 12 wherein the individualized encryption software decrypts the first three dimensional structure $X_2Y_1Z$ into numeric coordinate values.

14. The security system according to claim 13 wherein the individualized encryption software decrypts the two dimensional structure having X and Y numeric coordinate values, leaving the X numeric value.

15. The security system according to claim 14 wherein the individualized encryption software decrypts the X numeric value and removes the steganography from the file such that only the amino acid base layer remains having the XO value, provide the XO value such that the recipient can open the file that has been decrypted after having entered the proper index number, the X, $X_1Y$, $X_2Y_1Z$, $X_3Y_2Z_1$ numeric coordinate values and K value.

16. A method for improving the security of a file sent by a user having a special purpose user computer to a recipient having a recipient special purpose computer, the method comprising the steps of:

providing an individualized encryption software application server;

providing the special purpose user computer that is in communication with the individualized encryption software application server by way of transport layer security, and the file to be sent from the special purpose user computer to the recipient special purpose computer;

providing the individualized encryption software application server with individualized encryption software that includes individualized management software;

the individualized management software scans the unencrypted file and generates metadata, and a metadata file, a record file and an associated index number;

providing a security system database for storing the metadata file, the record file and the index number;

providing the individualized encryption software with individualized management software that scans the file and determines the number of natural and synthetic amino acids required to encode an amino acid base layer, and the amino acid base layer is in the form of an amino acid linear chain made of the natural and synthetic amino acids and has a length designated XO;

the individualized management software includes a secure amino acids generator program and providing an amino acid database for storing natural amino acids and synthetic amino acids data, and the individualized management software sends a request to the secure amino acids generator program that randomly selects natural and synthetic amino acids from the amino acids database, and the secure amino acid database generator generates the mathematical characteristics of the natural and synthetic amino acids;

the individualized management software includes a steganography program and steganography is applied to the file, and the individualized management software merges the file with the linear amino acid linear chain having a length (XO) and outputs an X value;

the individualized management software includes a secret key generator for generating a secret key having a K value; the individualized encryption software processes the X value into a two dimensional structure having X1 and Y numeric coordinate values that are saved in a record file database;

the individualized encryption software mathematically folds the two dimensional structure into a first three dimensional structure and generates $X_2Y_1Z$ numeric coordinate values, and the $X_2Y_1Z$ numeric coordinate values are saved in the record file database;

the individualized encryption software mathematically folds the first three dimensional structure into a second three dimensional structure and generates $X_3Y_2Z_1$ numeric coordinate values, and the $X_3Y_2Z_1$ numeric coordinate values are saved in the record file database;

wherein the file is encrypted with the index number, the X value, the secret key value K, the $X_1Y$ numeric coordinate values, the $X_2Y_1Z$ numeric coordinate values, and the $X_3Y_2Z_1$ numeric coordinate values and the encrypted file can be sent from the special purpose user computer to the recipient special purpose computer; and wherein the index number, the $X_1Y$ numeric coordinate values, the $X_2Y_1Z$ numeric coordinate values, and the $X_3Y_2Z_1$ numeric coordinate values and the secret key with K value function as a password such that if the recipient enters the correct values for each, then the individualized encryption software allows the file to be decrypted.

17. The method according to claim 16 wherein the individualized management software determines an amino acid count number of the natural and synthetic amino acids that are needed for encrypting the file, the individualized management software includes an individualized encryption software rules program that is programmed to follow first order rules, and each time the natural and synthetic amino acids are randomly selected from the secure amino acid database the individualized encryption software rules program processes the natural and synthetic amino acid data to determine if any first order rules are violated by the selection of these natural and synthetic amino acids.

18. The method according to claim 17 wherein the individualized encryption software rules program executes the first order rules such that each time the natural and synthetic amino acids are selected they are processed to determine if there is any duplication of natural and synthetic amino acids in the amino acid base layer and if there is duplication of natural and synthetic amino acids in the amino acid base layer then a new amino acid base layer is automatically generated by the individualized encryption software rules program until there is no duplication of the natural and synthetic amino acids in the amino acid base layer, and selecting natural and synthetic amino acids from the secure amino acid database such that the total number of natural and synthetic amino acids are ⅓ natural amino acids and ⅔ synthetic amino acids and if this ratio is not achieved, then the individualized encryption software rules program selects different natural and synthetic amino acids until there are ⅓ natural amino acids and ⅔ synthetic amino acids.

19. The method according to claim 18 further includes sending the index number, the X, $X_1Y$, $X_2Y_1Z$, $X_3Y_2Z_1$ numeric coordinate values and the K value from the special purpose user computer to the recipient special purpose computer, and wherein the recipient inputs the index number, the X, $X_1Y$, $X_2Y_1Z$, $X_3Y_2Z_1$ numeric coordinate values and the K value and if the values are incorrect then the recipient receives a null message and in the event of a null message the individualized management software generates different index number, the X, $X_1Y$, $X_2Y_1Z$, $X_3Y_2Z_1$ numeric coordinate values and the K values for the recipient to input and if they are the correct values then the file can be accessed.

* * * * *